United States Patent [19]
Shiba et al.
[11] 3,936,303
[45] Feb. 3, 1976

[54] PHOTOGRAPHIC PHOTOSENSITIVE ELEMENT AND DEVELOPING METHOD THEREOF

[75] Inventors: Keisuke Shiba; Seiiti Kubodera; Hideki Naito; Takeshi Hirose, all of Minami-ashigara, Japan

[73] Assignee: Fuji Photo Film Co., Ltd., Minami-ashigara, Japan

[22] Filed: July 3, 1974

[21] Appl. No.: 485,655

[30] Foreign Application Priority Data
July 3, 1973 Japan .............................. 48-75126

[52] U.S. Cl. ............................ 96/74; 96/22; 96/55; 96/100; 96/120; 260/340
[51] Int. Cl.$^2$ ... G03C 1/76; G03C 7/16; C07D 3/17
[58] Field of Search ............... 96/3, 74, 100, 22, 97, 96/55, 120; 260/340

[56] References Cited
UNITED STATES PATENTS

| | | | |
|---|---|---|---|
| 2,322,027 | 6/1943 | Jelley et al. | 96/74 X |
| 3,431,107 | 3/1969 | Weyerts | 96/3 |
| 3,676,137 | 7/1972 | Mizuki et al. | 96/56.5 |

*Primary Examiner*—David Klein
*Assistant Examiner*—Alfonso T. SuroPico
*Attorney, Agent, or Firm*—Sughrue, Rothwell, Mion, Zinn & Macpeak

[57] ABSTRACT

A silver halide photographic photosensitive element having a hydrophilic colloidal layer prepared by dispersing photographic additives in a fatty oil which is liquid at room temperature; which boils at temperatures higher than 250°C under atmospheric pressure; which is soluble in water in a proportion of less than about 10% by weight at 25°C; and which dissolves water in a proportion of less than about 5% by weight at 25°C, and a developing method thereof.

19 Claims, No Drawings

PHOTOGRAPHIC PHOTOSENSITIVE ELEMENT AND DEVELOPING METHOD THEREOF

BACKGROUND OF THE INVENTION

1. Field of the Invention

The present invention relates to photographic photosensitive elements which can be produced and developed without using organic materials which tend to cause environmental pollution, and a developing method thereof. More particularly, the present invention relates to photographic photosensitive members which are produced by dispersing photographic additives in specific fatty oils.

2. Description of the Prior Art

Heretofore, an oil-soluble coupler has been dissolved in an appropriate organic solvent having a high boiling point and dispersed in a gelatin solution in the presence of a surface active agent, and the resulting mixture has been used as a silver halide photographic emulsion. In this case, phthalic ester based compounds and phosphoric ester based compounds have been used as the high boiling organic solvent.

Nowadays, these types of solvents are used in preparing most color photographic photosensitive elements in which oil-soluble incorporated type couplers are used.

Other various kinds of compounds are known as the high boiling organic solvent, which are described, for example, in U.S. Pat. Nos. 2,322,027, 2,533,514, and 3,287,134; German Pat. No. 1,152,610; and British Patent No. 1,272,561.

The phthalic ester based compounds and phosphoric ester based compounds, however, are considered to be the most excellent compounds of the known compounds with respect to dispersion capability of a coupler, affinity to a gelatin-colloid layer, influence on the stability of a color formed, chemical stability in photosensitive materials, low price, etc.

The phthalic ester based compounds and phosphoric ester based compounds do not have any harmful action on the human body even in contact therewith if they are contained in a photographic photosensitive element. However, there is a possibility that they cause environmental pollution at the time of producing a photosensitive element or when the photosensitive element is abandoned after the developing treatment.

To the incorporated type color photographic photosensitive element, antioxidants such as the so-called "DIR-hydroquinone" are added alone or in combination with a coupler or other additives for the purpose of preventing color mixing due to the diffusion of an oxidized color forming developer, improving the image quality, preventing the formation of fog at the time of color forming development, preventing the formation of stain, improving the stability of the formed color image, etc. Most of these antioxidants are dispersed in phthalic ester based compounds or phosphoric ester based compounds. The antioxidants also must possess properties such as excellent dispersion capability in solvents, high reactivity with the reaction product of the color forming developer, high chemical stability, etc.

The incorporated type color photographic photosensitive element and the black and white photographic photosensitive element generally contain filter dyes and fluorescent brightening agents for absorbing visible light or ultraviolet light for the purpose of improving color reproduction and color sharpness, and stabilizing the color image, in addition to the antioxidant for preventing the oxidation of photosensitive nuclei, the latent image or the silver image.

For the filter dyes and fluorescent brightening agents, phthalic ester based compounds and phosphoric ester based compounds are often used as a solvent. N-dialkyl substituted alkylamide compounds as disclosed in U.S. Pat. No. 3,502,474 are used as the solvent for filter dyes and fluorescent brightening agents, but they have the drawback that a bad odor often remains. Although Japanese Pat. Laid-open No. 14322/1973 describes that biphenyl derivatives can be used as a high boiling organic solvent, biphenyl derivatives can not be employed for the reason that they cause environmental pollution.

SUMMARY OF THE INVENTION

Accordingly, the present invention removes the abovedescribed drawbacks.

An object of the present invention is to provide photographic photosensitive elements which can be produced without using any harmful materials.

Another object of the present invention is to provide photographic photosensitive elements which are produced by dispersing photographic additives such as couplers, filter dyes or antioxidants in high boiling organic solvents which are not harmful and do not cause any environmental pollution after being a discarded.

A further object of the present invention is to provide photographic photosensitive elements which permit a reduction of environmental pollution at the time of development.

A still further object of the present invention is to provide photographic photosensitive elements wherein high boiling solvents are used which can provide a more excellent image quality than with phthalic ester based compounds or phosphoric ester based compounds.

These and other objects and advantages will be apparent from the following description of the invention.

The objects of the present invention can be attained by a photosensitive element in which the photographic additives are dispersed in a hydrophilic colloid using fatty oils which are liquid at room temperature (at 25°C), which fail at temperatures higher than 250°C under atmospheric pressure, which are soluble in water in a proportion less than about 10% by weight, and which dissolve water in a proportion less than about 5% by weight.

DETAILED DESCRIPTION OF THE INVENTION

The fatty oils which can be used in the present invention satisfy the following requirements:

1. They are liquid at room temperature;
2. Their boiling point is higher than about 250°C under ordinary pressure (a pressure of one atmosphere);
3. Their solubility in water (at 25°C) is less than about 10% by weight; and
4. Their water dissolving capacity of the fatty oil (e.g., the amount of water which can be dissolved in the oil) is less than about 5% by weight.

Aliphatic esters of glycerin and derivatives thereof, alkyl esters of aliphatic dicarboxylic acids and derivatives thereof, and alkyl esters of aliphatic tricarboxylic acids and derivatives thereof are particularly useful as the fatty oils. It is preferred that these ester portions contain not more than 8 carbon atoms, e.g., about 1 to about 8 carbon atoms.

Preferred compounds for use in the present invention are those represented by the general formulae (I), (II) and (III):

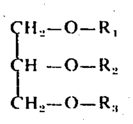

(I)

wherein $R_1$, $R_2$ and $R_3$, which may be the same or different, each is an acyl group containing about 2 to 8 carbon atoms, such as acetyl, propionyl, ethoxycarbonyl, butyloyl, hexanoyl, octanoyl, acetoacetyl, 2-butenoyl, butoxypropionyl, phenylacetyl, and the like; and at least one of $R_1$ and $R_3$ can be

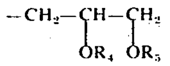

wherein $R_4$ and $R_5$, which may be the same or different, each are the same group as defined for $R_2$;

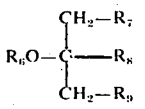

(II)

wherein $R_6$ is the same as defined for $R_2$; $R_7$, $R_8$ and $R_9$, which may be the same or different, each is an alkoxycarbonyl group containing not more than 8 carbon atoms, such as methoxycarbonyl, ethoxycarbonyl, propoxycarbonyl, allyloxycarbonyl, benzyloxycarbonyl and the like; and $$R_{10}-CH_2-(CH_2)_n-CH_2-R_{11} \quad (III)$$

wherein $R_{10}$ and $R_{11}$ are the same as defined for $R_7$ and *n* is an integer of 1 to 6.

Representative examples of the fatty oils of the present invention are shown in the Table below together with the properties thereof although the present invention is not to be interpreted as being limited thereto. In the Table, A indicates the physical state at 25°C, B indicates the solubility in water at 25°C (% by weight), C indicates the amount of water which can be dissolved, and D indicates the boiling point at atmospheric pressure.

Table

| | A | B | C | D |
|---|---|---|---|---|
| (1) Glycerol Triacetate $(CH_3CO-OCH_2)_2CHO.COCH_3$ | liquid | 7 | 5 | above 250°C |
| (2) Glycerol Tripropionate $C_3H_5(O-CO-C_2H_5)_3$ | do | 0.3 | below 0.1 | do |
| (3) Glycerol Tributyrate $C_3H_5(O-CO-C_3H_7)_3$ | do | below 0.1 | do | do |
| (4) Glycerol Monolaulate Triacetate | do | 3 | do | do |
| (5) Tributyl Citrate $(C_4H_9O-CO-CH_2)_2C(OH)CO-OC_4H_9$ | do | below 0.1 | do | do |
| (6) Acetyl Triethyl Citrate $(C_2H_5O-COC-CH_2)_2C(O-COCH_3.)CO-OC_2H_5$ | do | 0.7 | do | do |
| (7) Acetyl Tri-n-butyl Citrate $(C_4H_9O-CO-CH_2)_2-C(O-COCH_3.)CO-OC_4H_9$ | do | below 0.1 | do | do |
| (8) Di-2-ethyloxy Adipate $C_8H_{17}O-CO-(CH_2)_4COOC_8H_{17}$ | do | do | 0.1 | do |
| (9) Dioctyl Sebacate $C_8H_{17}O-CO-(CH_2)_8CO-OC_8H_{17}$ | do | do | below 0.1 | do |

The high boiling organic solvents of the present invention are characterized in that they are substantially harmless and hardly cause environmental pollution. Moreover, the high boiling solvents of the present invention are superior over phthalic ester based compounds, e.g. dibutyl phthalate, and phosphoric ester based compounds, e.g. tricrecyl phosphate, with respect to dispersion property and color image stability. These matters will be understood from the Examples described hereinafter.

As photographic additives which can be dispersed in a hydrophilic colloid using the high boiling solvents of the present invention, all of the compounds which have been dispersed in the hydrophilic colloid using conventional high boiling solvents can be employed. Representative additives are couplers which are coupling-reactable with the oxidation product of an aromatic primary amine color forming developer; antioxidants for preventing color-fog and oxidation of the formed color image due to the oxidation product of the aromatic primary amine color forming developer; filter dyes or ultraviolet absorbers for selectively absorbing visible light or ultraviolet light, etc.

Couplers as used herein include those compounds which are capable of forming color upon color forming development using aromatic primary amine developers such as phenylenediamine derivatives, aminophenol derivatives, and the like. For instance, examples of such couplers are 5-pyrazolone couplers, cyanoacetyl cumarone couplers, open chain acylacetonitrile couplers, acylacetamide couplers such as the benzoylacetanilides and the pivaloylacetanilides, naphthol couplers, phenol couplers and the like.

In greater detail, as magenta couplers, 5-pyrazolone couplers, cyanoacetyl cumarone couplers, indazolone couplers and the like can be used. The couplers represented by the general formula (IV) are particularly useful.

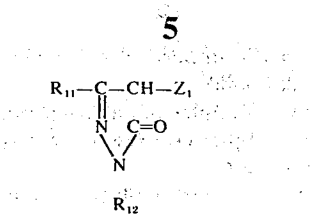

(IV)

wherein $R_{11}$ is an alkyl group selected from the group consisting of a primary, secondary, or tertiary alkyl group, such as methyl, propyl, n-butyl, t-butyl, hexyl, 2-hydroxyethyl, 2-phenylethyl and the like; an aryl group; a heterocyclic group such as quinolinyl, pyridyl, benzofuranyl, oxazolyl, and the like; an amino group such as methylamino, diethylamino, phenylamino, tolylamino, 4-(3-sulfobenzamino)anilino, 2-chloro-5-acylaminoanilino, 2-chloro-5-alkoxycarbonylanilino, 2-trifluoromethylphenylamino and the like; a carbonamido group such as alkylcarbonamido such as ethylcarbonamido, arylcarbonamido, heterocyclic carbonamido such as benzothiazolylcarbonamido, sulfonamido, heterocyclic sulfonamido and the like; or a ureido group such as alkylureido, arylureido, heterocyclicureido and the like; and $R_{12}$ is an aryl group such as naphthyl, phenyl, 2,4,6-trichlorophenyl, 2-chloro-4,6-dimethylphenyl, 2,6-di-chloro-4-methoxyphenyl, 4-methylphenyl, 4-acylaminophenyl, 4-alkylaminophenyl, 4-trichloromethyl phenyl, 3,5-dibromophenyl, and the like; or a heterocyclic group such as benzofuranyl, naphthooxazolyl, quinolinyl, and the like; and $Z_1$ is a hydrogen atom or a group which is removable at color development, such as acyloxy, aryoxy, halogen, thiocyano, disubstituted amino, allyloxycarbonyloxy, alkoxycarbonyloxy, benzotriazolyl, indazolyl, arylazo, heterocyclic azo, and the like. These compounds are described in U.S. Pat. Nos. 3,227,550, 3,252,924, 3,311,476, and 3,419,391; German Pat. Laid-open (OLS) No. 2,015,867; and U.S. Pat. application Ser. No. 471,639, filed May 20, 1974.

Arylmonothio groups such as 2-aminophenylthio, 2-hydroxycarbonylphenylthio and the like; heterocyclic monothio groups such as tetrazolyl, triazinyl, triazolyl, oxazolyl, oxadiazolyl, diazolyl, thiazyl, thiadiazolyl and the like; heterocyclic imido groups such as 1-benzotriazolyl, 1-indazolyl, 2-benzotriazolyl, and the like, etc., which liberate development inhibitors at the time of development, can be also used for $Z_1$. These compounds are described in U.S. Pat. Nos. 3,148,062, 3,227,554, 3,615,506 and 3,701,783.

Yellow couplers are open chain acylacetamide couplers such as pivaloylacetanilide coupler, benzoylacetanilide coupler, and the like; open chain acylacetonitrile coupler; and like. The compounds represented by the following general formula (V) are particularly useful.

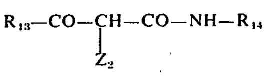

(V)

wherein $R_{13}$ is a primary alkyl, secondary alkyl, or tertiary alkyl group such as t-butyl, 1,1-dimethylpropyl, 1,1-dimethyl-1-methoxyphenoxymethyl and the like; or an aryl group such as phenyl, alkylphenyl, e.g. 3-methylphenyl, 3-octadecylphenyl, alkoxyphenyl, e.g. 2-methoxyphenyl, 4-methoxyphenyl, halophenyl, 2-halo-5-alkamidophenyl, e.g. 2-chloro-5-[α-(2,4-di-tert-amylphenoxy)butylamido]phenyl, 2-methoxy-5-alkamidophenyl, 2-chloro-5-sulfonamidophenyl, and the like; and $R_{14}$ is an aryl group such as 2-chlorophenyl, 2-halo-5-alkamidophenyl, e.g. 2-chloro-5-[α-(2,4-di-tert-amylphenoxy)acetamido]phenyl, 2-chloro-5-(4-methylphenylsulfonamido)phenyl, 2-methoxy-5-(2,4-di-tert-amylphenoxy)acetamidophenyl; and $Z_2$ is a hydrogen atom or a group which is removable at color development. Examples of removable groups are halogen atoms, particularly fluoride, and acyloxy, aryloxy, heterocyclic carbonyl, oxy, sulfimido, alkylsulfoxy, aryl, sulfoxy, phthalimido, dioxoimidazolyzinyl, dioxooxazolyzynyl, indazolyl, dioxothiazolyzyl and like groups. These compounds are described in U.S. Pat. Nos. 3,227,550, 3,253,924, 3,277,155, 3,265,506, 3,408,194 and 3,415,652; French Patent No. 1,411,384; British Pat. Nos. 944,490, 1,040,710 and 1,118,028; and German Pat. Laid-open (OLS) Nos. 2,057,941, 2,163,812, 2,213,461 and 2,219,971.

Arylmonothio groups such as phenylthio, 2-carboxyphenylthio, and the like; heterocyclic thio groups; 1-benzotriazol groups; 1-benzodiazole groups; and the like, which liberate development inhibitors, can also be used as $Z_2$. Particularly, the groups as described in U.S. Pat. application Ser. No. 454,525 filed Mar. 25, 1974 can be used.

The cyan coupler is, for example, a naphthol coupler or a phenol coupler. The couplers represented by the following general formulae (VI) and (VII) are particularly useful.

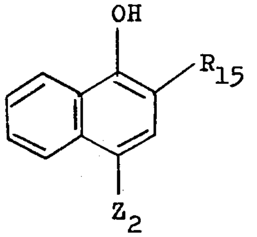

(VI)

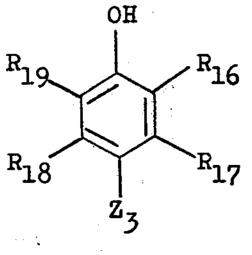

(VII)

wherein $R_{15}$ is a substituent as used in cyan couplers such as a carbamyl group, e.g. alkylcarbamyl, aryl carbamyl, such as phenyl carbamyl, heterocyclic carbamyl such as benzothiazolylcarbamyl and the like; a sulfamyl group, e.g. alkylsulfamyl, arylsulfamyl such as phenylsulfamyl, heterocyclic sulfamyl, and like; an alkoxycarbonyl group; an aryloxy-carbonyl group or the like; and $R_{16}$ is an alkyl group; an aryl group; a heterocyclic group, an amino group such as amino, alkylamino, arylamino and the like; a carbonamido group such as alkylcarbonamido, arylcarbonamido and the like; a sulfonamido group; a sulfmamyl group such as alkylsulfamyl, arylsulfamyl and the like; a carbamyl group or the like; and $R_{17}$, $R_{18}$ and $R_{19}$ are the same as described for $R_{16}$, and also a halogen atom, or an alkoxy group;

and $Z_3$ is a hydrogen atom or a group which is removable at color development such as those defined for $Z_2$. $Z_3$ can be a halogen atom such as chloro, bromo, iodo, and the like, or an indazolyl, heterocyclic imido, acyloxy, allyloxy, alkoxy, sulfo, arylazo, heterocyclic azo, or the like group. These compounds are described in U.S. Pat. Nos. 2,423,730, 3,227,550 and 3,311,476; and British Pat. Nos. 1,084,480 and 1,165,563; etc.

The coupler of the present invention can be colored coupler. Colored couplers are described in U.S. Pat. Nos. 2,983,608, 3,005,712 and 3,034,892; British Pat. Nos. 936,621, 1,269,073, 586,211 and 627,814; and French Pat. Nos. 980,372, 1,091,903, 1,257,887, 1,398,308 and 2,015,649; etc.

The couplers as used in the present invention are preferably diffusion-resistant. To render the coupler diffusion-resistant, groups containing hydrophobic radicals of about 8 to 32 carbon atoms are introduced in the molecule. These groups are called ballast groups. The ballast group can be connected to the coupler nucleus directly or through an imino, ether, carbonamido, sulfonamido, ureido, ester, imido, carbamoyl, sulfamoyl, or like bond.

Representative examples of ballast groups are shown in the specific examples couplers of the present invention given hereinafter.

The following are representative examples of the ballast groups.

(I) Alkyl and alkenyl groups
e.g., $-CH_2-CH(C_2H_5)_2$, $-C_{12}H_{25}$, $-C_{16}H_{33}$, $-C_{17}H_{33}$, etc.

(II) Alkoxyalkyl groups
e.g., $-(CH_2)_3-O-(CH_2)_7CH_3$,

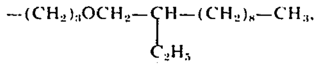

etc.
as described in Japanese Patent Publication No. 27563/1964.

(III) Alkylaryl groups e.g.,

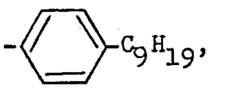

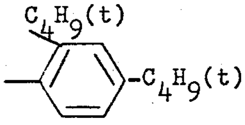

, etc.

(IV) Alkylaryloxyalkyl groups e.g.,

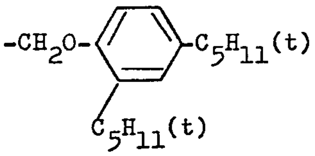

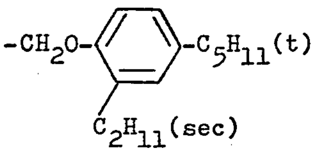

,

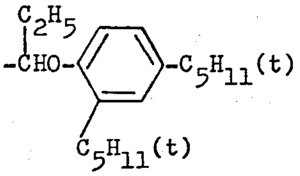

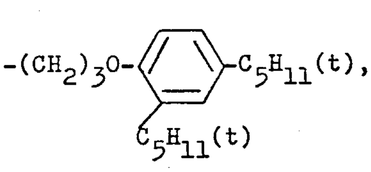

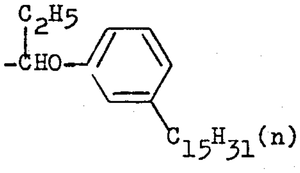

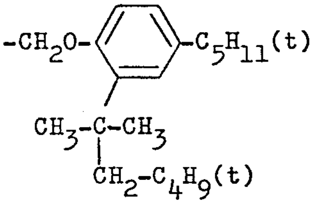

,

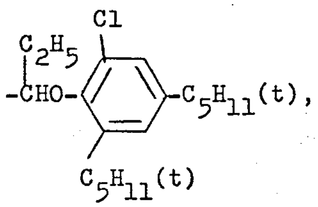

, etc.

(V) Acylamidoalkyl groups e.g., 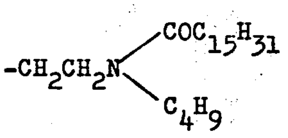 , 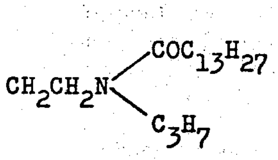 ,

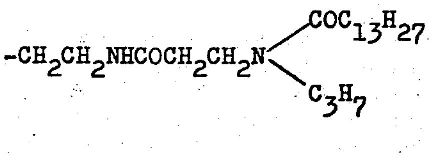

as described in U.S. Pat. Nos. 3,333,344 and 3,418,129.

(VI) Alkoxyaryl and aryloxyaryl groups e.g., 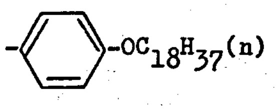 , 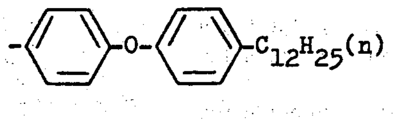

(VII) Groups containing long chain aliphatic groups such as alkyl or alkenyl group and groups such as carboxy or sulfo groups which are water-solubilizing groups e.g., 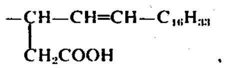 , 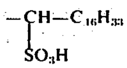 , etc.

(VIII) Ester substituted alkyl groups e.g., 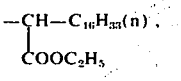 , $-CH_2-CH_2-COOC_{12}H_{25}(n)$, etc.

Yellow Couplers (1) a-{3-[α-(2,4-di-tert-aminophenoxy)-butyramido]benzoyl}-2-methoxyacetanilide (2) α-Acetoxy-α-3-[γ-(2,4-di-tert-amylphenoxy)-butyramido]-benzoyl-2-methoxyacetanilide (3) N-(4-Anisoylacetamidobenzenesulfonyl)-N-benzyl-N-toluidine (4) α-(2,4-Dioxo-5,5-dimethyloxazolyzinyl)-α-pivaloyl-2-chloro-5-[α-(2,4-di-tert-aminophenoxy)-butyramido]acetanilide (5) α-(4-Carboxyphenoxy)-α-pivaloyl-2-chloro-5-[α-(2,4-di-tert-amylphenoxy)butyramido]acetanilide (6) α-[3-(1-Benzyl-2,4-di-oxo)hydrantoin]-α-pivaloyl-2-chloro-5-[α-2,4-di-tert-amylphenoxy)-butyramido]acetanilide (7) α-Benzoyl-α-(2-benzothiazolythio)-4-[N-(γ-phenylpropyl)-N-4-tolyl)sulfamyl]acetanilide (IX) Aryl or heterocyclic group substituted alkyl groups e.g., 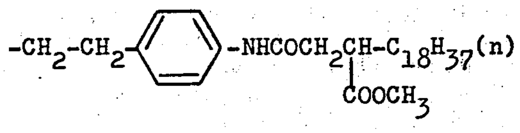

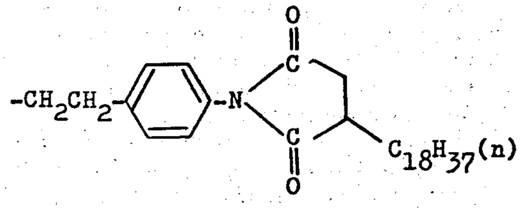 , etc.

(X) Aryloxyalkoxycarbonyl substituted aryl groups e.g., 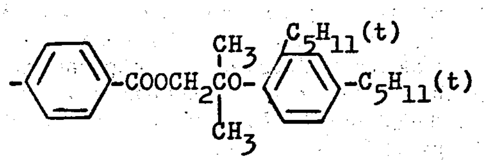

The following are representative examples of the present invention although the present invention is not to be construed as being limited thereto.

(8) α-Pivaloyl-α-(5- or 6-bromo-1-benztriazole-5-[α-(2,4-di-tert-amylphenoxy)propionamido]-2-chloroacetanilide Magenta Couplers (9) 1-(2,4,6-Trichlorophenyl)-3-[3-(2,4-di-tert-amylphenoxyacetamido)benzamido]-5-pyrazolone

(10) 1-(2,4,6-Trichlorophenyl)-3-{3-[α-(2,4-di-tert-amylphenoxy)acetamido]benzamido}-4-acetoxy-5-pyrazolone

(11) 1-(2,4,6-Trichlorophenyl)-3-dodecylamido-4-(4-hydroxyphenyl)azo-5-pyrazolone

(12) 1-(2,4,6-Trichlorophenyl)-3-[(3-tridecanoylamino-6-chloro)anilino]-5-pyrazolone

(13) 1-(2,4,6-Trichlorophenyl)-3-(3-tetradecyloxycarbonyl-6-chloro)anilino-4-(1-naphthylazo)-5-pyrazolone

(14) 1-(2,4-Dichloro-6-methoxyphenyl)-3-[(3-tridecanoylamino-6-chloro)anilino]-4-benzyloxycarboxy-5-pyrazolone

(15) 1-14-[γ-(2,4-Di-tert-aminophenoxybutyramido)phenyl]-3-piperidinyl-4-(1-phenyl-5-tetrazolylthio)-5-pyrazolone

(16) 1-(2,4,6-Trichlorophenyl)-3-{4-[α-(2,4-di-tert-amylphenoxy)butyramido]anilino}-4-(1-phenyl-5-tetrazolylthio)-5-pyrazolone

(17) 1-{4-[α-(2,4,-Di-tert-aminophenoxy)acetamido]phenyl}-3-methyl-4-(5- or 6-bromo-1-benztriazole)-5-pyrazolone Cyan Couplers

(18) 1-Hydroxy-N-[γ-(2,4-di-tert-aminophenoxypropyl)]-2-naphthamide

(19) 1-Hydroxy-4-[2-(2-hexyldecyloxycarbonyl]-2-[N-(1-naphthyl)]naphthamide

(20) 1-Hydroxy-4-chloro-N-[α-(2,4-di-tert-amylphenoxy)butyl]-2-naphthamide

(21) 5-Methyl-4,6-dichloro-2-[α-(3-n-pentadecylphenoxy)butyramido]phenol

(22) 1-Hydroxy-4-iodo-N-dodecyl-2-naphthamide

(23) 5-Methoxy-2-[α-(3-n-pentadecylphenoxy)-butyramido]-4-(1-phenyl-5-tetrazolylthio)phenol Non-color Forming Coupler

(24) N-[α-(2,4-Di-tert-amylphenoxy)acetyl]-ω-(1-phenyl-5-tetrazolylthio)-m-aminoacetophenone Antifading agents for the formed color image such as those agents as described in U.S. Pat. Nos. 3,764,337 and 3,432,300 and German Pat. Laid-open (OLS) No. 2,146,668 can be dispersed in the solvents of the present invention together with the couplers.

Antioxidants as used in the present invention include phenol, hydroquinone or precursors thereof having an aliphatic group containing 8 or more carbon atoms such as those antioxidants as described in U.S. Pat. Nos. 2,336,327, 2,728,659, 2,835,579 and 3,700,453.

The filter dyes which can be used in the present invention include oleophilic oxonol dyes, benzotriazole based ultraviolet absorbents, and benzophenone based ultraviolet absorbents such as those compounds as described in U.S. Pat. Nos. 3,253,921, 3,533,794, 3,794,493, 3,785,827, and 3,707,375, etc.

As the antioxidants for the formed color image, the compounds as described in U.S. Pat. Nos. 3,432,300 and 3,764,337, German Pat. Laid-open (OLS) No. 2,146,668 are useful. The compounds represented by the formulae (VIII) (IX) and (X) are particularly useful.

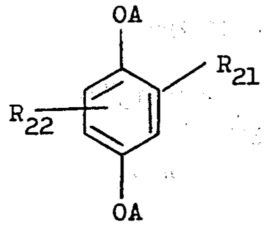

(VIII)

wherein $R_{21}$ is a straight or branched chain alkyl group containing 8 to 20 carbon atoms; $R_{22}$ is a hydrogen atom or a straight or branched chain alkyl group containing 8 to 20 carbon atoms; and A is a hydrogen atom or a group which is removable with alkali, such as an acyl group (e.g., acetyl), an alkoxycarbonyl group, and the like. The benzene nucleus can be substituted with other alkyl groups containing 8 or less carbon atoms, halogen or thelike;

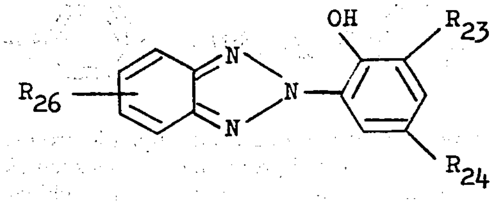

(IX)

wherein $R_{23}$ and $R_{24}$ each is a hydrogen atom or an alkyl group containing 5 or less carbon atoms; and $R_{25}$ is a hydrogen atom, an alkoxy group, or a halogen atom;

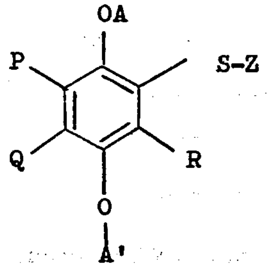

(X)

wherein P, Q and R each is a hydrogen atom; an alkyl group such as methyl, allyl, ethyl, octyl, dodecyl and the like; a hydroxy group such as methoxy, ethoxy, etc.; an amino group; an alkylthio group such as nonylthio, tridecylthio, and the like; an arylthio group; an aryl group such as phenyl, tolyl, and the like; a halogen atom; or a heterocyclic group such as tetrazolyl, thiazolyl, quinolynyl; and the S-Z moiety is tetrazolylthio, thiazolylthio, or the like; and P and Q can combine to form a carbon containing ring; and A and A' each is a hydrogen atom or a group which is removable with alkali, such as an acyl group, an alkoxycarbonyl group or the like; and Z is a heterocyclic group which is substantially photographically inert and is removable at development, such as tetrazolyl, e.g. 1-phenyltetrazolyl, 1-alkoxyphenyltetrazolyl, and the like; triazolyl, e.g. 1-phenyl-3-n-amyl-1,2,4-triazolyl; thiadiazolyl, e.g. 5-methylthiothiadiazolyl, 5-propylthiadiazolyl and the like; oxazolyl, e.g. 4-methyloxazolyl, benzooxazolyl, α-naphthoxazolyl and the like; oxadiazolyl; thiazolyl; pyrimidyl, or the like.

The high boiling solvents of the present invention can be used in combination with substantially water-insoluble low boiling auxiliary solvents such as methyl acetate, ethyl acetate, butyl acetate, and the like or water-soluble organic auxiliary solvents such as methyl isobutyl ketone, β-ethoxy ethyl acetate, methyl carbitol, methyl cellusolve, dipropylene glycol, dimethyl formamide, dioxane or the like. These solvents are described in U.S. Pat. Nos. 2,801,170, 2,801,171, 2,949,360 and 2,835,579. These auxiliary solvents can be removed by washing as described in U.S. Pat. Nos. 2,801,171, 2,949,360 and 3,396,027 or can be removed by evaporation as described in U.S. Pat. Nos. 2,322,027 and 2,801,171; and German Pat. Laid-open (OLS) No. 2,045,464.

Solutions which are prepared by dispersing photographic additives such as couplers, antioxidants, and filter dyes in the high boiling solvent of the present invention, either alone or in combination with auxiliary solvents, are dispersed in hydrophilic colloids, particularly aqueous solutions of gelatin. The dispersion procedures are described, for example, in U.S. Pat. Nos. 2,304,939; 2,322,027; 2,801,170; 2,801,171 and 2,949,360.

As auxiliary dispersion agents, commonly used anionic surface active agents such as sodium alkylbenzene sulfonate, sodium octylsulfosuccinate, sodium dodecyl sulfonate, sodium alkylnaphthalene sulfonate, Fischer type couplers and the like; amphoteric surface active agents such as N-tetradecyl-N,N-dipolyethylene-α-betaine, and the like; and nonionic surface active agents such as sorbitan monolaurate can be used. A suitable amount of the auxiliary dispersing agent can range from about 1/50 to 1/2 parts by weight of the high boiling solvent.

Of the anionic surface active agents used as the auxiliary dispersion agent, alkylbenzene sulfonic acid based compounds and alkylnaphthalene sulfonic acid based compounds are generally used.

Those anionic surface active agents represented by the general formula (XI) are preferably used for the dispersion in which the high boiling solvents of the present invention are used.

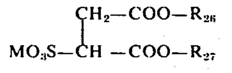
(XI)

wherein $R_{26}$ and $R_{27}$ each is a straight or branched chain alkyl group containing 4 to 20 carbon atoms; and M is a cation such as a sodium ion, potassium ion, ammonium ion, onium cation or the like.

The compounds represented by the general formula (XI) disperse a solution (oil droplet) and stabilize the colloid to the same extent as or greater than with the conventionally used alkanol B (a sodium alkylnaphthalene sulfonate produced by E. I. du Pont de Nemours and Co.) or alkylbenzene sulfonic acid. Moreover, they do not exert any harmful action on the human body.

Those anionic surface active agents represented by the general formula (XII) are also usable.

$$R_{28}-(O)_p-SO_3M \quad (XII)$$

wherein $R_{28}$ is an aliphatic group including a straight or branched chain alkyl group containing 6 to 20 carbon atoms; and *p* is 0 or 1; and M is the same as defined for M of the general formula (XI). Suitable aliphatic groups include octyl, decyl, dodecyl, octadecyl, 5-methylhexyl,

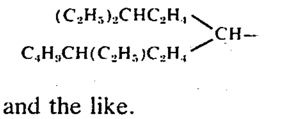 , 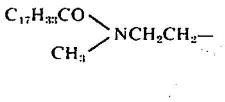

and the like.

An unexpected effect can be obtained using a dispersion which is prepared by dispersing photographic additives such as a coupler, an antioxidant and a filter dye in the high boiling solvent of the present invention.

German Pat. No. 1,152,610 describes the use of mixed glycerine esters of natural higher aliphatic acids. These esters, however, are deficient in disperability and color density as compared with phthalic ester based compounds and phosphoric ester based compounds. Moreover, when used as an industrial starting material, they suffer from a drawback that a photographically unifrom quality cannot be maintained. Thus, these esters are different from the high boiling solvents of the present invention with respect to their chemical structure and moreover, they are quite inferior over the solvents of the present invention in the photographic properties.

British Pat. No. 1,272,561 describes the use of a water-in-soluble wax. This wax is obviously different from the solvents of the present invention in view of the descriptions in the specification, in *Rikagaku Jiten*, 3rd., page 1465 Yuwanami Shoten (1971) and in Tatsuo Karikome *Shokubutsu Seibun No Kagaku* (Chemistry of Plant Components) 7th, Chapter 6, Nanazndo (1962). That is, the solvents of the present invention are different from waxs in that they are esters of lower aliphatic acids and tthat they are always liquid at room temperature.

U.S. Pat. No. 2,322,027 describes various high boiling solvents. However, neither the solvents of the present invention nor the objects of the present invention are disclosed in this U.S. Patent.

The silver halide emulsions which can be used in the present invention, are photographic emulsions comprising silver halides such as silver bromide, silver iodide, silver chloride, or mixtures thereof, e.g. silver chlorobromide, silver iodobromide, and silver chloroiodobromide. When at least one layer of the photographic emulsion layers contains silver chloroiodide silver iodobromide or silver chloroiodobromide with an iodide content of about 1 to 10 mol%, good results can be obtained.

The hydrophilic colloids which can be used in the present invention include gelatin, cellulose derivatives, alginates, hydrophilic synthetic polymers such as polyvinyl alcohol, polyvinyl pyrrolidone, polystyrene sulfonic acid and the like, plasticizers for improving the dimensional stability of the film, polymer latexs such as polymethyl methacrylate, polyethyl acrylate and the like, etc.

To the silver halide emulsions as used in the present invention conventionally used chemical sensitizing procedures can be applied. For instance, gold sensitization as described in U.S. Pat. Nos. 2,399,083, 2,597,856 and 2,597,915; reduction sensitization as described in U.S. Pat. Nos. 2,487,850 and 2,521,925; sulfur sensitization as described in U.S. Pat. Nos. 1,623,499 and 2,410,698; sensitization using different metal ions as described in U.S. Pat. Nos. 2,448,060, 2,566,245 and 2,566,263; and combinations of the above mentioned processes can be employed.

The silver halide photographic emulsions which can be used in the present invention can be used in combination with conventional optical sensitizers, for example, a cyanine dye or a merocyanine dye as described in U.S. Pat. Nos. 2,526,632; 2,503,776; 2,493,748; 3,384,486; 2,933,390 and 2,937,089, such as anhydro-9-methyl-5,5′-dimethyl-3,3′-di(3-sulfopropyl)benzcarboncyanine, 5,5′-dichloro-9-ethyl-di(2-hydroxyethyl)-thiacarbocyanine bromide, anhydro-5,5′-diphenyl-9-ethyl-3,3′-di(2-sulfoethyl)benzoxazolocarbocyanine hydroxide and the like, and they may be sensitized with sensitizing dyes for use in spectral sensitization of color photosensitive materials alone or in admixture with each other.

The silver halide emulsions which can be used in the present invention can contain conventionally used stabilizers such as 4-hydroxy-1,3,3a,7-tetrazaindene derivatives and the like; antifog agents such as mercapto compounds, benzotriazole derivatives, and the like; auxiliary coating agents such as saponin, sodium alkylbenzene sulfonates, and the like; hardening agents such as formaldehyde, mucobromic acid, 2,4-dichloro-6-hydroxy-s-triazone sodium salt and the like; wetting agents and sensitizing agents such as onium derivatives, e.g., the tertiary ammonium salts as described in U.S. Pat. Nos. 2,271,623, 2,288,226; and 2,334,864 and e.g. polyalkyleneoxide derivatives as described in U.S. Pat. Nos. 2,708,162, 2,531,832, 2,533,990, 3,210,191, and 3,158,484; etc. Moreover, irradiation preventing dyes can be included and a filter layer, a mordant dyeing layer, or a colored layer containing a hydrophobic dye can be provided as a constituent of the color photosensitive element of the present invention.

The photosensitive emulsions as used herein can be coated on various kinds of supports. As the support, cellulose acetate film, polyethylene terephthalate film, polyethylene film, glass plate, baryta paper, resin laminated paper, synthetic paper can be used.

For the photographic photosensitive elements of the present invention, developers are used which can reduce silver halide particle to silver at the time of color image formation. In the case of black and white photography, developers mainly containing polyhydroxy benzenes, N-alkylaminophenols, 1-phenyl-3-pyrazolidones, or mixtures thereof can be used.

Examples of polyhydroxy benzenes include hydroquinone, pyrocatechol, pyrogallol, and the like. Examples of N-alkylaminophenols are N-methylaminophenol, N-ethylaminophenol and the like; and of the 1-phenyl-3-pyrazolidones include 1-phenyl-3-pyrazolidone, 1-phenyl-4,4-dimethyl-3-pyrazolidone and the like.

In the case of color forming development, developers mainly containing of para-phenylene diamine derivatives such as 4-amino-N,N-diethylaniline, 4-amino-3-methyl-N-methyl-N-($\beta$-methylsulfonamidoethyl)aniline, 4-hydroxyaniline, 4-hydroxy-2,6-dibromoaniline and the like, can be used.

The photographic photosensitive elements of the present invention can be processed at ordinary temperatures, e.g. 20° to to 30°C and it is also possible to process the elements at higher temperatures, e.g. about 30° to 60°C or higher.

Preferred procedures for processing the color photosensitive elements of the present invention are described in Japanese Pat. Publication No. 35749/1970, Japanese Pat. Application Nos. 67798/1969, 13313/1971 and 19516/1971; H. Gordon *The British Journal of Photography*, 558 (Nov. 15, 1954), ibid, 440 (Sept. 9, 1955), ibid., 2 (Jan. 6, 1956); S. Horwitz *The British Journal of Photography*, 212 (Apr. 22, 1960); E. Gehret *The British Journal of Photography*, 396 (May 7, 1965), J. Meech *The British Journal of Photography*, 182 (Apr. 3, 1959); German Patent Laid-open (OLS) No. 2,238,051, etc.

Various techniques for removing or reducing the causes of environmental pollution must be used at the development.

First, benzyl alcohol having a development accelerating action which is usually contained in a color forming developer, causes the biological oxygen demand (BOD) to be increased. When the solvents of the present invention are used in combination with couplers wherein hydroxyl or carboxylic acid is used as the ballast and removable group (for example, $Z_1$, $Z_2$, or $Z_3$ of general formulae (IV), (V) or (VI) ), a sufficiently rapid development rate can be obtained and an excellent color image can be obtained without using benzyl alcohol.

Secondly, ferricyanide or ferrocyanide, which is contained in a bleaching solution for the reduced silver, causes the harmful cyan ion to be produced, and chelate agents of oxidizable metal salts render the treatment of waste water to be difficult.

In the color photographic photosensitive elements wherein the solvents of the present invention are used, the silver image obtained and reduced silver can be easily bleached. Thus, the color photographic photosensitive elements can be advantageously used for preventing pollution.

The oxidation-reduction potential ($E_{redox}$) as defined hereinafter of the silver bleaching solutions used with the color photographic photosensitive elements ranges from about −150 mv to 1000 mv the elements and can be silver-bleached with a bleaching solution containing halide ion and metal salts or organic oxidants. Examples of metal salts are transition metal salts, particularly salts or complex salts of $Ti^{4+}$, $V^{5+}$, $Cr^{6+}$, $Mn^{7+}$, $Mn^{3+}$, $Cu_2^+$, $Fe^{3+}$, $Co_3^+$ and like; and the organic oxidants are p-sulfophenyl quinone, sulfonaphthoquinone, Brewster Blue radical, Weitz-radical and the like. These compounds are described in U.S. Pat. Nos. 2,507,183, 2,529,981, 2,625,477, 2,748,000, 2,810,648 and 2,705,201; British Pat. Nos. 1,111,313, 777,635, 1,032,024, 1,014,396 and 982,984; and Japanese Pat. Publication Nos. 14035/1970 and 13944/1971, etc.

"$E_{redox}$" as used herein is measured as follows.

The measurement was carried out using a conjugated platinum electrode (EA-216; manufactured by Metrohm Ltd.) equipped with silver/silver chloride electrode and a potentiometer (E-436; manufactured by Metrohm Ltd.) at 25°C±0.2°C. The test results are shown below.

Bleaching-Fixing Solution used in Example 3
pH=6.8 $E_{redox}$=−30 mV
Bleaching Solution
pH=1.5 $E_{redox}$=720 mV
Potassium Bromide 20 g
Ferric Chloride 41.5 g
(hexahydrate)

To the resulting mixture is added water to prepare 1 liter of an aqueous solution.

The following examples are given to illustrate the invention in greater detail. Unless otherwise indicated, all parts, percents, ratios and the like are by weight.

EXAMPLE 1

A solution prepared by heating at 60°C a mixture of 10 g of Coupler (21), 10 ml of Compound (3) of the present invention as a high boiling solvent, 20 ml of ethyl acetate, and 2 ml of a 20% solution of sorbitol laurate in methanol was added to 100 ml of an aqueous solution at 60°C which contained 10 g of gelatin, 0.5 g of sodium di-2-ethylhexyl sulfosuccinate and 0.7 g of phenol. The resulting mixture was stirred vigorously mechanically with a homogenizer to prepare a coupler Emulsion (1).

The above procedure was repeated except that 10 ml of Compound (7), 10 ml of di-n-butylphthalate and 10 g of glycerol tri-n-stearate were used in place of Compound (3) to prepare Emulsion (2), and Comparison Emulsions (A) and (B), respectively.

These emulsions were cooled to about 5°C and stored at this temperature and the variation in the particle size of the oil droplet and the amount of the coupler precipitated were measured. The results obtained are shown in Table 1.

Table 1

STABILITY OF EMULSIONS

| Emulsions | Particle Size just after Dispersion | Particle Size after Storage at 5°C for 14 Days | Amount of Precipiate after Storage at 5°C for 14 Days |
|---|---|---|---|
| | ($\mu$)* | ($\mu$)* | (mg)** |
| (1) | 0.19 | 0.20 | 3.5 |
| (2) | 0.21 | 0.21 | 4.0 |
| (A) | 0.21 | 0.22 | 5.5 |
| (B) | 0.27 | 0.30 | 8.5 |

*About 0.3 g of an emulsion was added to 100 ml of hot water and the average particle size of the resulting mixture was measured using a light-scattering method.
**10 g of an emulsion was precisely weighed, diluted with hot water three times, and suction-filtered using Toyo filter paper No. 5-B (produced by Toyo Roshi Co., Ltd.). The residue on the filter paper was weighed.

The results in Table 1 show that the oil droplets contained in Emulsions (1) and (2) were finer than those contained in Comparison Emulsions (A) and (B), and that the particle size of the droplets contained in Emulsions (1) and (2) changed little during storage. Moreover, the amount of the coupler precipitated during storage was small and a stable emulsion could be obtained.

EXAMPLE 2

The procedure of Example 1 was repeated except that 10 g of Coupler (4) was used in place of Coupler (21) and that 2 ml of Compound (3), 2 ml of Compound (7), 2 ml of di-n-butylphthalate, and 2 g of glycerol tri-n-stearate were used as a high boiling solvent to prepare Emulsions (3) and (4), and Comparison Emulsions (C) and (D), respectively.

The stability of the emulsions is shown in Table 2.

Table 2

STABILITY OF EMULSIONS

| Emulsions | Particle Size just after Dispersion | Particle Size after Storage at 5°C for 14 Days | Amount of Precipitate after Storage at 5°C for 14 Days |
|---|---|---|---|
| | ($\mu$) | ($\mu$) | (mg) |
| (3) | 0.14 | 0.16 | 1.3 |
| (4) | 0.17 | 0.17 | 1.4 |
| (C) | 0.16 | 0.21 | 1.6 |
| (D) | 0.17 | 0.26 | 2.7 |

The results show that the solvents of the present invention markedly stabilize an emulsion as compared with conventional high boiling solvents and wax.

EXAMPLE 3

The procedure of Example 1 was repeated except that 10 g of Coupler (12) was used in place of Coupler (21), and that 2 ml of Compound (3), 2 ml of Compound (7), 2 ml of di-n-butyl phthalate and 2 g of glycerol tri-n-stearate were used as a high boiling solvent to prepare Emulsions (5) and (6), and Comparison Emulsions (E) and (F), respectively.

36.8 g of Emulsion (5) was mixed with 80 g of a photographic emulsion containing 3.17 × $10^{-2}$ mol of silver chloride bromide (silver bromide: 95 mol%; silver chloride; 5 mol%) and 6.5 g of gelatin, to which 4 ml of a 2% methanol solution of 5-methyl-7-hydroxy-1,3,4,7a-tetrazaindene, 6.4 ml of a 2% aqueous solution of potassium polystyrene sulfonate, 8 ml of a 1% solution of sodium di-2-ethylhexyl sulfosuccinate and 8 ml of a 2% aqueous solution of 2-hydroxy-4,6-dichloro-S-triazine sodium salt were added. After adjusting the pH to 6.5, the mixture was coated on a cellulose triacetate film in a dry thickness of 6.2 $\mu$ to prepare Film (5). The Film (5) contained 1.63 × $10^{-3}$ mol of the coupler and 1.3 × $10^{-2}$ mol of silver chloride bromide.

The above procedure was repeated using Emulsions (6), (E), and (F) to prepare Films (6), (E), and (F), respectively.

These Films were subjected to stepwise exposure and then developed using Color Developer (a) containing benzyl alcohol or Color Developer (b) not containing benzyl alcohol.

| (I) | Color Development Steps | | |
|---|---|---|---|
| 1. | Color Development | 30°C | 6 minutes |
| 2. | Washing | " | 2 minutes |
| 3. | Bleaching Fixing | " | 1½ minutes |
| 4. | Washing | " | 2 minutes |
| 5. | Stabilizing | " | " |
| 6. | Washing | " | " |
| 7. | Drying | | |

The compositions of Color Developers (a) and (b) were as follows.

| (II) | Color Developer (a) | |
|---|---|---|
| | Benzyl Alcohol | 12.0 ml |
| | Diethylene Glycol | 3.5 ml |
| | Sodium Hydroxide | 2.0 g |
| | Sodium Sulfite (anhydrous salt) | 2.0 g |
| | Potassium Bromide | 0.4 g |
| | Sodium Chloride | 1.0 g |
| | Borax | 4.0 g |
| | Sodium Trinitroacetate | 1.6 g |
| | Hydroxylamine Sulfate | 2.0 g |
| | 4-(N-ethyl-N-methanesulfonamidoethyl) amino-2-methyl Aniline Sesquisulfate | 4.3 |

These ingredients were mixed and diluted with water to prepare 1000 ml of Color Developer (a).

(III) Color Developer (b)

Color developer (b) was prepared by excluding only benzyl alcohol from the ingredients of Color Developer (a).

(IV) Bleaching Fixing Solution

| (IV) | Bleaching Fixing Solution | |
|---|---|---|
| | Ethylenediamine Tetraacetic Acid Ferric Salt | 40.0 g |
| | Ammonium Thiosulfate (70%) | 150.0 ml |
| | Sodium Sulfite (anhydrous) | 12.0 g |

These ingredients were mixed and diluted with water to prepare 1000 ml of the solution.

| (V) | Stabilizing Solution | |
|---|---|---|
| | Sodium Benzoate | 0.5 g |
| | Glacial Acetate Acid | 13.0 ml |
| | Citric Acid (dihydrate) | 4.2 g |
| | Sodium Citrate (dihydrate) | 3.9 g |

These ingredients were mixed and diluted with water to prepare 1000 ml of the stabilizing solution.

The photographic properties of the thus-obtained films are shown in Table 3.

Table 3

| | Films | | | |
|---|---|---|---|---|
| | (5) | (6) | (E) | (F) |
| Color Developer (a) | | | | |
| Fog | 0.5 | 0.5 | 0.5 | 0.5 |
| Gamma | 3.1 | 3.3 | 3.1 | 3.0 |
| Relative Sensitivity | 100 | 100 | 100 | 87 |
| Maximum Color Forming Density | 3.09 | 3.21 | 3.08 | 2.91 |
| Color Developer (b) | | | | |
| Fog | 0.6 | 0.4 | 0.6 | 0.7 |
| Gamma | 2.2 | 2.1 | 2.2 | 1.9 |
| Relative Sensitivity* | 80 | 80 | 79 | 56 |
| Maximum Color Forming Density | 3.09 | 2.98 | 2.79 | 2.49 |

Note:
*The relative sensitivity is the reciprocal of the exposure amount required for providing a density of fog +1.0.

The results of Table 3 show that high sensitivity and high maximum color forming density can be obtained without reducing the gradation by using the high boiling solvents of the present invention. Particularly, in the case of using the color developer not containing benzyl alcohol, the reduction of sensitivity and maximum color forming density is small as compared with the comparison examples.

EXAMPLE 4

Emulsion (1) (59.2 g) of Example 1 was coated in the same manner as shown in Example 3 in a dry thickness of 3.1 $\mu$ to prepare Film (1). The film contained $1.63 \times 10^{-3}$ mole of the coupler per square meter of the film.

The above procedure was repeated using Emulsion (A) to obtain Film (A).

These films were exposed and developed in the same manner as in Example 3.

The films so developed were stored in a dark place at 60°C and at a relative humidity of 75% for 20 days, and the image density thereof was measured. The results obtained are shown in Table 4 as the image density reduction ratio (%) relative to the initial image density.

Table 4

COLOR IMAGE STABILITY (Image Density Reduction Ratio %)

| | Color Development | | | | | |
|---|---|---|---|---|---|---|
| | Color Developer (a) | | | Color Developer (b) | | |
| Films | Initial Image Density | | | Initial Image Density | | |
| | 0.5 | 1.0 | 2.0 | 0.5 | 1.0 | 2.0 |
| (1) | 0 | 3 | 5 | 0 | 1 | 2 |
| (A) | 2 | 7 | 10 | 1 | 2 | 5 |

The results show that the high boiling solvents of the present invention provide an image of high stability to high temperature and humidity.

EXAMPLE 5

Emulsion (4) (89.6 g) of Example 2 was coated in the same manner as shown in Example 3 in a dry thickness of 3.1 $\mu$ to prepare Film (4). The film contained $1.63 \times 10^{-3}$ mole of the coupler and $6.5 \times 10^{-3}$ mole per square meter of the film.

The above procedure was repeated using Emulsion (c) to obtain Film (C).

These films were exposed and developed in the same manner as in Example 3.

The films so developed were exposed through an ultraviolet filter for substantially removing ultraviolet light having a wavelength below 400 mm to a daylight fluorescent lamp having an illumination intensity of about 100,000 lux for 10 days and the image density thereof was measured. The light stability is shown in terms of the image density reduction ratio (%) in Table 5.

Table 5

| | Color Development | | | | | |
|---|---|---|---|---|---|---|
| | Color Developer (a) | | | Color Developer (b) | | |
| Films | Initial Image Density | | | Initial Image Density | | |
| | 0.5 | 1.0 | 2.0 | 0.5 | 1.0 | 2.0 |
| (4) | 3 | 10 | 12 | 3 | 7 | 12 |
| (C) | 4 | 12 | 15 | 6 | 9 | 15 |

It can be seen from these results that the high boiling solvents of the present invention provide an image of high stability to light.

The techniques of the present invention can be applied to color negative photosensitive element, color reversal photosensitive elements, color direct positive type photosensitive elements, transparent color positive photosensitive element, color papers, photosensitive elements for diffusion transfer process, color X-ray photosensitive elements, monochromatic industrial photographic elements, etc. Where antioxidants and filter dyes are used, the techniques of the present invention are applicable to black and white photosensitive elements and unconventional photosensitive element, for example, thermodevelopable materials.

While the invention has been described in detail and with reference to specific embodiments thereof, it will be apparent to one skilled in the art that various changes and modifications can be made therein without departing from the spirit and scope thereof.

What is claimed is:

1. A silver halide photographic photosensitive element comprising a hydrophilic colloidal layer having dispersed therein photographic additives in a fatty oil which:

is liquid at room temperature;

boils at temperatures higher than 250°C under atmospheric pressure;

is soluble in water in a proportion of about 10% by weight or less; and dissolves water in a proportion of about 5% by weight or less, said fatty oil being selected from the group consisting of the compounds of the general formula (I)

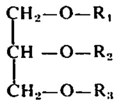 (I)

wherein $R_1$, $R_2$, and $R_3$, which can be the same or different, each is an acyl group containing 8 or less carbon atoms, and where at least one of $R_1$ and $R_3$ may be

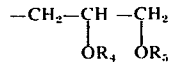

wherein $R_4$ and $R_5$, which can be the same or different, each is the same as $R_2$, or the fatty oil is selected from the group consisting of the compounds of the general formula (II):

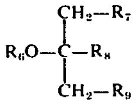 (II)

wherein $R_6$ is the same as $R_2$, and $R_7$, $R_8$, and $R_9$, which may be the same or different, each is an alkoxycarbonyl group containing 4 to 8 carbon atoms; or the fatty oil is selected from the group consisting of compounds of the general formula (III):

$$R_{10} - CH_2 - (CH_2)_n - CH_2 - R_{11} \qquad (III)$$

wherein $R_{10}$ and $R_{11}$ which may be the same or different, each is the same as $R_7$, and n is an integer of 1 to 6.

2. The photosensitive element according to claim 1, wherein $R_1$, $R_2$ and $R_3$ each is selected from the group consisting of an acetyl group, a propionyl group, an ethoxycarbonyl group, a butyryl group, a hexanoyl group, an octanoyl group, an acetacetyl group, a 2-butenoyl group, a butoxypropionyl group, and a phenylacetyl group.

3. The photosensitive element according to claim 1, wherein the fatty oil is glycerol triacetate.

4. The photosensitive element according to claim 1, wherein the fatty oil is glycerol tripropionate.

5. The photosensitive element according to claim 1, wherein the fatty oil is glycerol tributyrate.

6. The photosensitive element according to claiam 1, wherein the fatty oil is glycerol monolactate triacetate.

7. The photosensitive element according to claim 1, wherein the $R_7$ and $R_8$ each is, selected from the group consisting of a propoxycarbonyl group, an allyoxycarbonyl group, and a benzyloxycarbonyl group.

8. The photosensitive element according to claim 1, wherein the fatty oil is tributyl citrate.

9. The photosensitive element according to claim 1, wherein the fatty oil is acetyl tri-n-butyl citrate.

10. The photosensitive element according to claim 1, wherein the fatty oil is di-2-ethyloxy adipate.

11. The photosensitive element according to claim 1, wherein the fatty oil is dioctyl sebacate.

12. The photosensitive element according to claim 1, wherein the photographic additive comprises at least one color coupler.

13. The photosensitive element according to claim 12, wherein the coupler is selected from the group consisting of compounds of the general formula (IV):

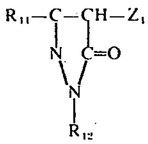 (IV)

wherein $R_{11}$ is an alkyl group, an aryl group, a heterocyclic group, an amino group, a carbonamido group, or a ureido; $R_{12}$ is an aryl group, or a heterocyclic group; and $Z_1$ is a hydrogen atom or a group removable on coupling with the oxidation product of a primary aromatic amino color developing agent.

14. The photosensitive element according to claim 12, wherein the coupler is selected from the group consisting of the compounds of the general formula (V):

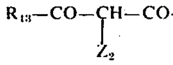 (V)

wherein $R_{13}$ is an alkyl group or an aryl group; $R_{14}$ is an aryl group; and $Z_2$ is a hydrogen atom or a group removable on coupling with the oxidation product of a primary aromatic amino color developing agent.

15. The photosensitive element according to claim 12, wherein the coupler is selected from the group consisting of the compounds of the general formula VI:

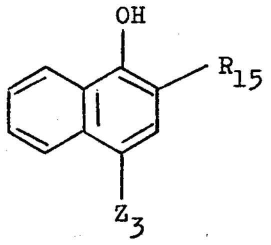 (VI)

wherein $R_{15}$ is a carbamyl group, a sulfamyl group, an alkoxycarbonyl group, or an aryloxycarbonyl group;

and $Z_3$ is a hydrogen atom or a group removable on coupling with the oxidation product of a primary aromatic amino color developing agent, and the compounds of the general formula (VII):

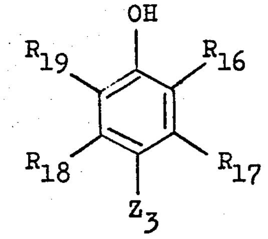
(VII)

wherein $R_{17}$, $R_{18}$, and $R_{19}$ which may be the same or different, each is the same as $R_{16}$; and $Z_3$ is an iodine atom or a group removable on coupling with the oxidation product of a primary amino color developing agent.

16. The photosensitive element according to claim 1, wherein the fatty oil is in combination with at least one auxiliary solvent.

17. The photosensitive element according to claim 16, wherein the auxiliary dispersing aid is selected from the group consisting of anionic surface active agents of the general formula (XI):

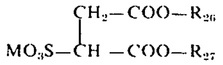
(XI)

wherein $R_{26}$ and $R_{27}$ which may be the same or different, each is a straight or branched chain alkyl group containing 4 to 20 carbon atoms; and M is a cation.

18. The photosensitive element according to claim 16, wherein the auxiliary dispersing aid is selected from the group consisting of anionic surface active agents of the general formula (XII):

$$R_{28}(O)_pSO_3M \quad (XII)$$

wherein $R_{28}$ is a straight or branched chain alkyl group containing 6 to 20 carbon atoms; and M is a cation.

19. A color photographic photosensitive element comprising 1. a hydrophilic colloid layer having dispersed therein at least one member selected from the group consisting of the compounds represented by the general formula (IV)

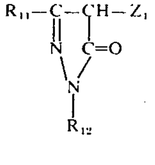
(IV)

wherein $R_{11}$ is an alkyl group, an aryl group, a heterocyclic group, an amino group, a carbonamido group, a sulfonamido, or an ureido group; $R_{12}$ is an aryl group or a heterocyclic group; and $Z_1$ is a hydrogen atom or a group removable on coupling with a primary aromatic amino color developing agent in at least one member selected from the group consisting of the fatty oils represented by the general formula (I)

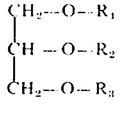
(I)

wherein $R_1$, $R_2$, and $R_3$, which may be the same or different, each is an acyl group containing 8 or less carbon atoms, and where at least one of $R_1$ and $R_3$ may be

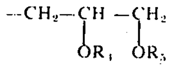

wherein $R_4$ and $R_5$, which may be the same or different, each is the same as $R_2$; the general formula (II)

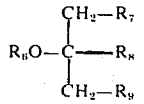
(II)

wherein $R_6$ is the same as $R_2$, and $R_7$, $R_8$, and $R_9$, which may be the same or different, each is an alkoxycarbonyl group containing 4 to 8 carbon atoms; and the general formula (III)

$$R_{10}-CH_2-(CH_2)_n-CH_2-R_{11} \quad (III)$$

wherein $R_{10}$ and $R_{11}$, which may be the same or different, each is the same as $R_7$, and $n$ is an integer of 1 to 6; in combination with at least one member selected from the group consisting of anionic surface active agents represented by the general formula (XI)

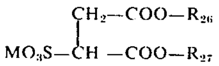
(XI)

wherein $R_{26}$ and $R_{27}$, which may be the same or different, each is a straight or branched chain alkyl group containing 4 to 20 carbon atoms; and M is a cation; and the general formula (XII)

$$R_{28}(O)_pSO_3M \quad (XII)$$

wherein $R_{28}$ is a straight or branched chain alkyl group containing 6 to 20 carbon atoms; $p$ is 0 or 1; and M is a cation;

2. a hydrophilic colloid layer having dispersed therein at least one member selected from the group consisting of the compounds represented by the general formula (V)

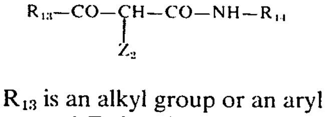
(V)

wherein $R_{13}$ is an alkyl group or an aryl group; $R_{14}$ is an aryl group; and $Z_2$ is a hydrogen atom or a group removable on coupling with the oxidation product of a primary aromatic amino color developing agent in at least one member selected from the group consisting of the fatty oils represented by the general formula (I),

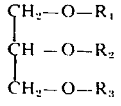
(I)

wherein $R_1$, $R_2$, and $R_3$, which may be the same or different, each is an acyl group containing 8 or less carbon atoms, and where at least one of $R_1$ and $R_3$ may be

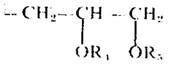

wherein $R_4$ and $R_5$, which may be the same or different, each is the same as $R_2$; the general formula (II)

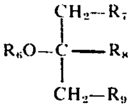 (II)

wherein $R_6$ is the same as $R_2$, and $R_7$, $R_8$, and $R_9$, which may be the same or different, each is an alkoxycarbonyl group containing 4 to 8 carbon atoms; and the general formula (III)

$$R_{10}-CH_2-(CH_2)_n-CH_2-R_{11} \quad \text{(III)}$$

wherein $R_{10}$ and $R_{11}$, which may be the same or different, each is the same as $R_7$, and n is an integer of 1 to 6; in combination with at least one member selected from the group consisting of anionic surface active agents represented by the general formula (XI)

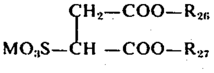 (XI)

wherein $R_{26}$ and $R_{27}$, which may be the same or different, each is a straight or branched chain alkyl group containing 4 to 20 carbon atoms; and M is a cation; and the general formula (XII)

$$R_{28}\text{-}(O)_p SO_3M \quad \text{(XII)}$$

wherein $R_{28}$ is a straight or branched chain alkyl group containing 6 to 20 carbon atoms; $p$ is 0 or 1; and M is a cation; and (3) a hydrophilic colloid layer having dispersed therein at least one member selected from the group consisting of the compounds represented by the general formula (VI) and (VII)

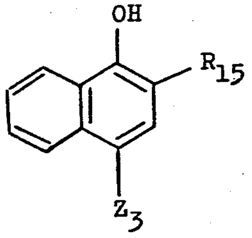 (VI)

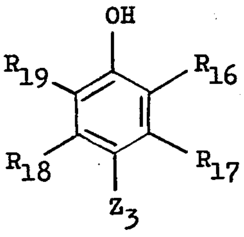 (VII)

wherein $R_{15}$ is a carbamyl group, a sulfamyl group, an alkoxycarbonyl group, or an aryloxycarbonyl group; and $Z_3$ is a hydrogen atom or a group removable on coupling with the oxidation product of a primary aromatic amino color developing agent; $R_{17}$, $R_{18}$, $R_{19}$ which may be the same or different, each is the same as $R_{16}$; and $Z_3$ is a group removable on coupling with the oxidation product of a primary aromatic amino color developing agent in at least one member selected from the group consisting of the fatty oils represented by the general formula (I)

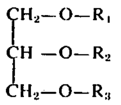 (I)

wherein $R_1$, $R_2$, and $R_3$, which may be the same or different, each is an acyl group containing 8 or less carbon atoms, and where at least one of $R_1$ and $R_3$ may be

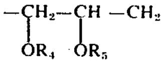

wherein $R_4$ and $R_5$, which may be the same or different, each is the same as $R_2$; the general formula (II)

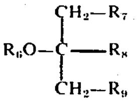 (II)

wherein $R_6$ is the same as $R_2$, and $R_7$, $R_8$, and $R_9$, which may be the same or different, each is an alkoxycarbonyl group containing 4 to 8 carbon atoms; and the general formula (III)

$$R_{10}-CH_2-(CH_2)_n-CH_2-R_{11} \quad \text{(III)}$$

wherein $R_{10}$ and $R_{11}$, which may be the same or different, each is the same as $R_7$, and $n$ is an integer of 1 to 6; in combination with at least one member selected from the group consisting of anionic surface active agents represented by the general formula (XI)

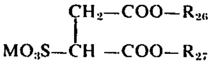 (XI)

wherein $R_{26}$ and $R_{27}$, which may be the same or different, each is a straight or branched chain alkyl group containing 4 to 20 carbon atoms; and M is a cation; and the general formula (XII)

$$R_{28}\text{-}(O)_p SO_3M$$

wherein $R_{28}$ is a straight or branched chain alkyl group containing 6 to 20 carbon atoms; $p$ is 0 or 1; and M is a cation.

* * * * *